US009278892B2

(12) United States Patent
Narula et al.

(10) Patent No.: US 9,278,892 B2
(45) Date of Patent: *Mar. 8, 2016

(54) CATALYTIC CONVERSION OF ALCOHOLS TO HYDROCARBONS WITH LOW BENZENE CONTENT (71) Applicant: UT-BATTELLE, LLC, Oak Ridge, TN (US)

(72) Inventors: Chaitanya K. Narula, Knoxville, TN (US); Brian H. Davison, Knoxville, TN (US); Martin Keller, Knoxville, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/263,257

(22) Filed: Apr. 28, 2014

(65) Prior Publication Data

US 2014/0322781 A1 Oct. 30, 2014

Related U.S. Application Data (63) Continuation of application No. 13/787,112, filed on Mar. 6, 2013.

(51) Int. Cl.
| | |
|---|---|
| *B01J 29/06* | (2006.01) |
| *C07C 1/20* | (2006.01) |
| *C07C 1/22* | (2006.01) |
| *B01J 29/18* | (2006.01) |
| *C07C 1/24* | (2006.01) |
| *C07C 2/66* | (2006.01) |
| *C07C 2/86* | (2006.01) |
| *B01J 29/08* | (2006.01) |
| *B01J 29/40* | (2006.01) |
| *B01J 29/80* | (2006.01) |
| *C07C 2/64* | (2006.01) |
| *C12P 7/06* | (2006.01) |
| *B01J 35/00* | (2006.01) |
| *B01J 29/48* | (2006.01) |
| *B01J 29/46* | (2006.01) |
| *B01J 29/70* | (2006.01) |
| *B01J 29/76* | (2006.01) |
| *B01J 29/78* | (2006.01) |

(52) U.S. Cl.
CPC ............ *C07C 1/22* (2013.01); *B01J 29/084* (2013.01); *B01J 29/18* (2013.01); *B01J 29/40* (2013.01); *B01J 29/80* (2013.01); *B01J 35/0006* (2013.01); *C07C 1/24* (2013.01); *C07C 2/64* (2013.01); *C07C 2/66* (2013.01); *C07C 2/864* (2013.01); *C12P 7/06* (2013.01); *B01J 29/061* (2013.01); *B01J 29/088* (2013.01); *B01J 29/405* (2013.01); *B01J 29/46* (2013.01); *B01J 29/48* (2013.01); *B01J 29/7049* (2013.01); *B01J 29/76* (2013.01); *B01J 29/78* (2013.01);

*B01J 2229/18* (2013.01); *B01J 2229/186* (2013.01); *C07C 2529/072* (2013.01); *C07C 2529/076* (2013.01); *C07C 2529/08* (2013.01); *C07C 2529/14* (2013.01); *C07C 2529/18* (2013.01); *C07C 2529/40* (2013.01); *C07C 2529/48* (2013.01); *C07C 2529/70* (2013.01); *Y02E 50/17* (2013.01)

(58) Field of Classification Search
USPC ............... 502/61, 64, 67, 71, 73, 77, 78, 79; 422/630; 585/322, 323, 407, 408
See application file for complete search history.

(56) References Cited

U.S. PATENT DOCUMENTS

| | | | |
|---|---|---|---|
| 3,702,886 A | 11/1972 | Agauer et al. | |
| 3,891,931 A * | 6/1975 | Nougaret et al. | ............. 327/343 |
| 3,894,107 A | 7/1975 | Butter et al. | |
| 3,899,544 A | 8/1975 | Chang et al. | |
| 3,928,483 A | 12/1975 | Chang et al. | |
| 3,931,349 A | 1/1976 | Kuo | |
| 3,969,427 A | 7/1976 | Bell et al. | |

(Continued)

FOREIGN PATENT DOCUMENTS

| | | |
|---|---|---|
| CN | 101454423 A | 6/2009 |
| DE | 98121148 A | 10/2000 |

(Continued)

OTHER PUBLICATIONS

U.S. Office Action dated Dec. 2, 2014 in U.S. Appl. No. 14/321,012.
International Search Report and Written Opinion dated Jul. 24, 2014 received from related International Application No. PCT/US2014/020154.
International Search Report and Written Opinion dated Oct. 30, 2014 received from International Application No. PCT/US2014/044999.
U.S. Office Action dated Oct. 21, 2014 in related U.S. Appl. No. 14/123,363.

(Continued)

*Primary Examiner* — Elizabeth Wood
(74) *Attorney, Agent, or Firm* — Scully, Scott, Murphy & Presser, P.C.

(57) ABSTRACT

A method for converting an alcohol to a hydrocarbon fraction having a lowered benzene content, the method comprising: converting said alcohol to a hydrocarbon fraction by contacting said alcohol, under conditions suitable for converting said alcohol to said hydrocarbon fraction, with a metal-loaded zeolite catalyst catalytically active for converting said alcohol to said hydrocarbon fraction, and contacting said hydrocarbon fraction with a benzene alkylation catalyst, under conditions suitable for alkylating benzene, to form alkylated benzene product in said hydrocarbon fraction. Also described is a catalyst composition useful in the method, comprising a mixture of (i) a metal-loaded zeolite catalyst catalytically active for converting said alcohol to said hydrocarbon, and (ii) a benzene alkylation catalyst, in which (i) and (ii) may be in a mixed or separated state. A reactor for housing the catalyst and conducting the reaction is also described.

12 Claims, 2 Drawing Sheets

(56) References Cited

U.S. PATENT DOCUMENTS

| | | | |
|---|---|---|---|
| 3,998,899 A | 12/1976 | Daviduk et al. | |
| 4,025,571 A | 5/1977 | Lago | |
| 4,035,430 A | 7/1977 | Dwyer et al. | |
| 4,058,576 A | 11/1977 | Chang et al. | |
| 4,071,573 A | 1/1978 | Owen et al. | |
| 4,138,440 A | 2/1979 | Chang et al. | |
| 4,148,835 A | 4/1979 | Chen et al. | |
| 4,278,565 A | 7/1981 | Chen et al. | |
| 4,289,606 A * | 9/1981 | Gladrow et al. | 208/120.1 |
| 4,338,475 A | 7/1982 | Pennington et al. | |
| 4,404,414 A | 9/1983 | Penick et al. | |
| 4,423,274 A | 12/1983 | Daviduk et al. | |
| 4,427,789 A | 1/1984 | Miale et al. | |
| 4,499,327 A | 2/1985 | Kaiser | |
| 4,524,234 A | 6/1985 | Kaiser | |
| 4,596,704 A | 6/1986 | Miale et al. | |
| 4,608,355 A | 8/1986 | Chu | |
| 4,727,214 A | 2/1988 | Uytterhoeven et al. | |
| 4,788,042 A | 11/1988 | Marsh et al. | |
| 4,788,369 A | 11/1988 | Marsh et al. | |
| 4,849,093 A | 7/1989 | Vauk et al. | |
| 4,861,937 A | 8/1989 | Baacke et al. | |
| 5,041,690 A | 8/1991 | Harandi et al. | |
| 5,045,287 A | 9/1991 | Harandi et al. | |
| 5,177,279 A | 1/1993 | Harandi | |
| 5,314,665 A | 5/1994 | Iwasa | |
| 5,491,270 A | 2/1996 | Chin et al. | |
| 5,773,676 A | 6/1998 | Drake et al. | |
| 5,993,642 A | 11/1999 | Mohr et al. | |
| 6,046,373 A | 4/2000 | Sun | |
| 6,323,383 B1 | 11/2001 | Tsuchida et al. | |
| 6,426,442 B1 * | 7/2002 | Ichikawa et al. | 585/469 |
| 7,438,868 B2 | 10/2008 | Kato | |
| 7,442,425 B2 | 10/2008 | Fu et al. | |
| 7,872,054 B2 | 1/2011 | Cortright et al. | |
| 7,927,551 B2 * | 4/2011 | Miyairi et al. | 422/168 |
| 2003/0171630 A1 | 9/2003 | Winder et al. | |
| 2005/0139517 A1 | 6/2005 | Waddick et al. | |
| 2007/0087934 A1 * | 4/2007 | Martens et al. | 502/214 |
| 2008/0103345 A1 | 5/2008 | Levin et al. | |
| 2008/0287720 A1 | 11/2008 | Clark | |
| 2009/0134065 A1 * | 5/2009 | Cheng et al. | 208/114 |
| 2010/0185033 A1 | 7/2010 | Karim et al. | |
| 2010/0270210 A1 * | 10/2010 | Long et al. | 208/120.01 |
| 2010/0304455 A1 | 12/2010 | Inoue et al. | |
| 2011/0061290 A1 | 3/2011 | Aulich et al. | |
| 2011/0152513 A1 | 6/2011 | Yao et al. | |
| 2013/0217935 A1 | 8/2013 | Adam et al. | |
| 2014/0148630 A1 | 5/2014 | Adam et al. | |
| 2014/0171691 A1 | 6/2014 | Kortan et al. | |
| 2014/0273146 A1 | 9/2014 | Narula et al. | |
| 2015/0011813 A1 | 1/2015 | Narula et al. | |

FOREIGN PATENT DOCUMENTS

| | | |
|---|---|---|
| DE | 10 2006 026 356 A1 | 12/2007 |
| DE | 2407778 C2 | 12/2010 |
| EA | 006785 B1 | 2/2005 |
| EA | 015812 B1 | 12/2011 |
| EP | 0 099 650 A1 | 2/1984 |
| EP | 0 130 368 A1 | 1/1985 |
| RU | 2 082 500 C1 | 6/1997 |
| RU | 2 425 091 C1 | 7/2011 |
| RU | 2 440 189 C1 | 1/2012 |
| WO | WO 90/12855 A1 | 11/1990 |
| WO | WO 2007/020068 A1 | 2/2007 |
| WO | WO 2007/112314 A2 | 10/2007 |
| WO | WO 2008/069841 A2 | 6/2008 |
| WO | WO 2008/069984 A2 | 6/2008 |
| WO | WO 2012/016787 A1 | 2/2012 |
| WO | WO 2012/174205 A1 | 12/2012 |
| WO | WO 2013/014081 A1 | 1/2013 |

OTHER PUBLICATIONS

U.S. Office Action dated Oct. 3, 2014 in related U.S. Appl. No. 14/293,248.

Hansen N. et al., "Theoretical Investigation of Benzene Alkylation With Ethene Over H-ZSM-5", *J. Phys. Chem. C 112(39)*:15402-15411 (2008).

Horňáček M. et al., "Alkylation of Benzene With 1-Alkenes Over Zeolite Y and Mordenite", *Acta Chimica Slovaca 2(1)*:31-45 (2009).

Liu K. et al., "Catalytic Role of Different Pore Systems in MCM-49 Zeolite for Liquid Alkylation of Benzene With Ethylene", *Journal of Catalysis* 283:68-74 (2011).

Process Economics Program (PEP), "The Production of Cumene Using Zeolite Catalyst", Marcus Ceasar, Oct. 8, 1999.

International Search Report and Written Opinion dated Sep. 27, 2012 received from related International Application No. PCT/US2012/042399.

Supplementary Extended European Search Report dated Nov. 24, 2014 received from EP Application No. 12799829.2.

U.S. Final Office Action dated Apr. 20, 2015 in U.S. Appl. No. 14/321,012.

English-language translation of the Office Action dated Nov. 15, 2014 received from the Chinese Patent Office in Application No. 201280036737.8.

Schulz J. et al., "Conversion of Ethanol Over Metal-Exchanged Zeolites", Chem. Eng. Technol. 16:332-337 (1993).

U.S. Final Office Action dated Jan. 27, 2015 in U.S. Appl. No. 14/293,248.

Office Action dated Dec. 15, 2015 received in related U.S. Patent Application, namely U.S. Appl. No. 13/787,112.

* cited by examiner

CATALYTIC CONVERSION OF ALCOHOLS TO HYDROCARBONS WITH LOW BENZENE CONTENT

CROSS REFERENCE TO RELATED APPLICATIONS

This application is a continuation of copending application Ser. No. 13/787,112 filed Mar. 6, 2013, all of the contents of which are incorporated herein by reference.

GOVERNMENT SUPPORT

This invention was made with government support under Prime Contract No. DE-AC05-00OR22725 awarded by the U.S. Department of Energy. The government has certain rights in the invention.

FIELD OF THE INVENTION

The present invention relates, generally, to the catalytic conversion of alcohols to hydrocarbons, and more particularly, to zeolite-based catalytic methods for such conversion.

BACKGROUND OF THE INVENTION

The conversion of alcohols to hydrocarbons is generally not commercially feasible. In fact, the majority of commercial alcohols are produced from hydrocarbons. Alcohol-to-hydrocarbon conversion is further prohibitive due to the significant cost requirements of current conversion processes. In particular, alcohol from natural means (e.g., by fermentation of biomass) would be a significantly more cost-efficient feedstock for a conversion process.

However, a major obstacle in applying current conversion methodology to biomass-produced alcohols (i.e., bio-alcohols) is the high concentration of water (and concomitant low alcohol concentrations) typically encountered in fermentation streams produced in biomass-to-alcohol refineries. Current alcohol-to-hydrocarbon conversion processes are generally incapable or highly ineffective in providing such conversion at such dilute alcohol and high water concentrations. Instead, current alcohol-to-hydrocarbon conversion processes generally require pure alcohol (i.e., in the substantial absence of water). Yet, concentration and/or distillation of alcohol from a fermentation stream to accommodate current technologies would be highly energy intensive, and thus, would largely offset gains made in the initial low cost of using a bio-alcohol.

Another significant obstacle in existing alcohol conversion processes is the unacceptably high level of benzene produced in the hydrocarbon fraction, generally up to about 5% benzene content. However, governing environmental regulations generally require a much lower benzene content for use as a fuel. For example, in the U.S., the Environmental Protection Agency (EPA) has recently imposed a benzene limit of 0.62 vol %. Thus, a further advantage would be provided by an alcohol conversion process that could produce a hydrocarbon blendstock with a substantially reduced benzene content.

SUMMARY OF THE INVENTION

In one aspect, the invention is directed to a method for catalytically converting an alcohol to a hydrocarbon or hydrocarbon fraction (i.e., mixture of hydrocarbons, or "hydrocarbon blendstock") that contains a reduced benzene content. In particular embodiments, the catalytic conversion is accomplished without requiring the alcohol to be purified or concentrated before the conversion reaction. For example, by methods described herein, effective conversion can be accomplished on dilute aqueous solutions of an alcohol, as found, for example, in the fermentation stream of a biomass fermentation reactor, to produce a hydrocarbon blendstock with a reduced benzene content.

In particular embodiments, the method includes contacting the alcohol, under conditions suitable for converting the alcohol to a hydrocarbon fraction, with a metal-loaded zeolite catalyst catalytically active for converting the alcohol to a hydrocarbon fraction, and contacting the produced hydrocarbon fraction with a benzene alkylation catalyst, under conditions suitable for alkylating benzene, to form alkylated benzene product in the hydrocarbon fraction. In a first particular embodiment, the method is practiced by contacting the alcohol with a catalyst mixture that includes the metal-loaded zeolite catalyst and benzene alkylation catalyst. In a second particular embodiment, the method is practiced by a two-step process, wherein, in a first step, the alcohol is contacted with the metal-loaded zeolite catalyst to form a hydrocarbon fraction, and in a second step, the produced hydrocarbon fraction is contacted with the benzene alkylation catalyst, wherein the metal-loaded zeolite catalyst and benzene alkylation catalyst are not mixed (i.e., separate).

In other aspects, the invention is directed to a catalyst composition that includes the metal-loaded zeolite catalyst and benzene alkylation catalyst as a mixture. In yet other aspects, the invention is directed to a one-zone or two-zone alcohol-to-hydrocarbon conversion reactor in which the catalyst composition is present as either a mixture or in separated form. In a particular embodiment of a two-zone reactor, a first zone contains the metal-loaded zeolite catalyst catalytically active for converting the alcohol to the hydrocarbon, and a second zone contains a benzene alkylation catalyst, wherein the two-zone reactor is constructed such that the alcohol passes through the first zone to form hydrocarbon, and the generated hydrocarbon passes into the second zone to reduce its benzene content. Additional reaction zones or processes, such as for fractionation or distillation into separate blendstocks, or for mixing into other blendstocks, may or may not also be included.

DETAILED DESCRIPTION OF THE INVENTION

As used herein, the term "about" generally indicates within ±0.5, 1, 2, 5, or 10% of the indicated value. For example, in its broadest sense, the phrase "about 100° C." can mean 100° C.±10%, which indicates 10010° C. or 90-110° C.

The term "alcohol", as used herein, can refer to a single alcohol or a mixture of two or more alcohols, and may also include aqueous solutions of one or more alcohols. The alcohol considered herein, to be converted to hydrocarbon, is primarily, but not necessarily only, one that can be produced by a fermentation process (i.e., a bio-alcohol). Most notable examples of bio-alcohols considered herein include ethanol, n-butanol (i.e., butanol), and isobutanol. In different embodiments, the alcohol can be ethanol, or butanol, or isobutanol, or a combination thereof, as commonly found in fermentation streams. Other alcohols include n-propanol, isopropanol, sec-butanol, t-butanol, n-pentanol, and isopentanol (isoamyl alcohol). In particular embodiments, the alcohol is an aqueous solution of alcohol (i.e., the alcohol is a component of an aqueous solution), as found in fermentation streams. In fermentation streams, the alcohol is typically in a concentration of no more than about 20% (vol/vol), 15%, 10%, or 5%. In some embodiments, a fermentation stream is directly contacted with the catalyst (typically, after filtration to remove solids) to effect the conversion of the alcohol in the fermentation stream. In other embodiments, the fermentation stream is concentrated in alcohol (for example, of at least or up to 20%, 25%, 30%, 40%, 50%, 60%, 70%, or 80%) before contacting the fermentation stream with the catalyst. In yet other embodiments, alcohol in the fermentation stream is selectively removed from the fermentation stream, such as by distillation, to produce a substantially pure form of alcohol as the feedstock (e.g., a concentration of at least 90% or 95% of alcohol). In still other embodiments, the alcohol is dewatered to near azeotropic ethanol (e.g., 92-94% ethanol) or completely dewatered into 100% alcohol before contacting with the catalyst.

The term "hydrocarbon", as used herein, can refer to a single hydrocarbon compound or a mixture of two or more hydrocarbon compounds. Although a wide variety of hydrocarbon product can be produced by the instant method, the hydrocarbon primarily considered herein is typically saturated, and more particularly, in the class of alkanes, which may be straight-chained, or branched, or a mixture thereof, particularly when the hydrocarbon product is to be used as a fuel. The alkanes particularly desired herein include those containing at least four, five, or six carbon atoms, and up to twelve, fourteen, sixteen, seventeen, eighteen, or twenty carbon atoms. Some examples of straight-chained alkanes include n-butane, n-pentane, n-hexane, n-heptane, n-octane, n-nonane, n-decane, n-undecane, n-dodecane, n-tridecane, n-tetradecane, n-pentadecane, n-hexadecane, n-heptadecane, n-octadecane, n-nonadecane, and n-eicosane. Some examples of branched alkanes include isobutane, isopentane, neopentane, isohexane, 3-methylpentane, 2,3-dimethylbutane, 2,2-dimethylbutane, 2-methylhexane, 3-methylhexane, 2,2-dimethylpentane, 2,3-dimethylpentane, 2,4-dimethylpentane, 3,3-dimethylpentane, 2-methylheptane, and 2,2,4-trimethylpentane (isooctane). Some other hydrocarbon products typically produced by the instant conversion method include olefins (i.e., alkenes, such as, for example, ethylene, propylene, n-butene, and/or isobutene) and aromatics (for example, naphthalene, benzene, toluene, and/or xylenes).

The hydrocarbon product particularly considered herein is a mixture of hydrocarbon compounds useful as a fuel or as a blendstock in a fuel. The mixture of hydrocarbon compounds produced herein preferably substantially corresponds (e.g., in composition and/or properties) to a known petrochemical fuel, such as petroleum, or a fractional distillate of petroleum. Some examples of petrochemical fuels include gasoline, kerosene, diesel, and jet propellant (e.g., JP-8). Like hydrocarbon fuel grades in current use, the mixture of hydrocarbon compounds produced herein can, in some embodiments, be predominantly or exclusively composed of alkanes, alkenes, aromatics, or a mixture thereof. The raw hydrocarbon product, produced by the instantly described method, is typically fractionated by distillation into different fuel grades, each of which is known to be within a certain boiling point range. A particular advantage of the instant method is its ability to produce such fuel grades in the substantial absence of contaminants (e.g., mercaptans) normally required to be removed during the petroleum refining process. Moreover, by appropriate adjustment of the catalyst and processing conditions, a select distribution of hydrocarbons can be obtained.

Depending on the final composition of the hydrocarbon product, the product can be directed to a variety of applications, including, for example, as precursors for plastics, polymers, and fine chemicals. The process described herein can advantageously produce a range of hydrocarbon products that differ in any of a variety of characteristics, such as molecular weight (i.e., hydrocarbon weight distribution), degree of saturation or unsaturation (e.g., alkane to alkene ratio), and level of branched or cyclic isomers. The process provides this level of versatility by appropriate selection of, for example, composition of the catalyst (e.g., catalytic metal), amount of catalyst (e.g., ratio of catalyst to alcohol precursor), processing temperature, and flow rate (e.g., LHSV).

The process described herein combines the use of an alcohol-to-hydrocarbon conversion catalyst (i.e., metal-loaded zeolite) and a benzene alkylation catalyst. As further described below, the method combines the two catalysts by using the two catalysts in either a mixed (combination) or unmixed (separated) state. In the context of the instant disclosure, the compositions of the two catalysts are different.

In one embodiment of the conversion method described herein, a two-stage process is employed. In the first stage, an alcohol is first catalytically converted to a hydrocarbon or hydrocarbon fraction by contacting the alcohol with a metal-loaded zeolite catalyst at conditions (particularly, temperature and choice of catalyst) suitable to effect said conversion. In the second stage, the produced hydrocarbon or hydrocarbon fraction is then contacted with a benzene alkylation catalyst, under conditions suitable for alkylating benzene, to form alkylated benzene product from benzene contained in the produced hydrocarbon fraction. Other aromatic compounds (e.g., toluene, xylenes, ethylbenzenes, and naphthalene) that may be present in the hydrocarbon fraction are generally also alkylated during the benzene alkylation process.

In the first and second stages, a suitable reaction temperature is independently employed during contact of the alcohol with the metal-loaded zeolite catalyst and then with contact of the hydrocarbon with the benzene alkylation catalyst. The temperature for each stage may be the same or different. Generally, the reaction temperature is at least 100° C. and up to 550° C. In different embodiments, the reaction temperature for each of the processes is precisely, about, at least, above, up to, or less than, for example, 100° C., 125° C., 150° C., 175° C., 200° C., 225° C., 250° C., 275° C., 300° C., 325° C., 350° C., 375° C., 400° C., 425° C., 450° C., 475° C., 500° C., 525° C., or 550° C., or a temperature within a range bounded by any two of the foregoing exemplary temperatures, e.g., 100° C.-550° C., 200° C.-550° C., 300° C.-550° C., 400° C.-550° C., 450° C.-550° C., 100° C.-500° C., 200° C.-500° C., 300° C.-500° C., 350° C.-500° C., 400° C.-500° C., 450° C.-500° C., 100° C.-450° C., 200° C.-450° C., 300° C.-450° C., 350° C.-450° C., 400° C.-450° C., 100° C.-425° C., 200° C.-425° C., 300° C.-425° C., 350° C.-425° C., 375° C.-425° C., 400° C.-425° C., 100° C.-400° C., 200° C.-400° C., 300° C.-400° C., 350° C.-400° C., and 375° C.-400° C.

Generally, ambient (i.e., normal atmospheric) pressure of about 1 atm is used at least for the conversion process described herein. However, in some embodiments, an elevated pressure or reduced pressure may be used for either the conversion or alkylation process. In typical embodiments, an elevated pressure is used in the alkylation process. In different embodiments, the elevated pressure may be, for example, 1.5, 2, 3, 4, 5, 10, 12, or 15 atm. In other embodiments, the pressure may be reduced to, for example, 0.5, 0.2, or 0.1 atm for either the conversion or alkylation process, or both.

The catalysts and reactor can have any of the designs known in the art for catalytically treating a fluid or gas at elevated temperatures, such as a fluidized bed reactor. The process may be in a continuous or batch mode. In particular embodiments, the alcohol is injected into a heated reactor such that the alcohol is quickly volatilized into gas, and the gas passed over the catalyst. In some embodiments, the reactor design includes a boiler unit and a reactor unit if the fermentation stream is used directly as a feedstock without purification. The boiler unit is generally not needed if the fermentation stream is distilled to concentrate ethanol because the distillation process removes the dissolved solids in the fermentation streams. The boiler unit volatilizes liquid feedstock into gases prior to entry into the reactor unit and withholds dissolved solids.

Additional reaction zones or processes may or may not also be included. For example, in some embodiments, the produced hydrocarbon blendstock, after, during, or prior to reaction with the alkylation catalyst, may be fractionated, distilled, or otherwise separated into narrower carbon range blendstocks. In other embodiments, the produced hydrocarbon blendstock, after, during, or prior to reaction with the alkylation catalyst, may be mixed with or into another hydrocarbon blendstock or mixed with an alkylating reactant (e.g., an olefin, such as ethylene, or an alkenyl chloride or alkyl chloride). In other embodiments, the hydrocarbon blendstock or a separated or purified portion thereof, after reaction with the alkylation catalyst, may be processed into a new product, such as a commercially or industrially relevant product derived from hydrocarbons, e.g., an alkane, alkene, alkylated benzene, polycyclic aromatic, alkylated polycyclic aromatic, or polymer. In yet other embodiments, the alcohol, prior or during contact with the metal-loaded zeolite catalyst, may be concentrated, purified (e.g., by distillation), or mixed with another alcohol or solvent (e.g., water). Any of the foregoing exemplary additional processes may be integrated into the instant process, typically, by interconnecting the apparatus necessary for the additional process with the apparatus necessary to practice the instant process.

In another embodiment of the conversion method described herein, a direct (single-stage or single-step) process is employed in which the alcohol is contacted with a mixture (combination) of the metal-loaded zeolite catalyst and benzene alkylation catalyst under suitable conditions to directly produce a hydrocarbon fraction reduced in benzene content. The term "mixture" or "combination" as used herein, generally indicates a solid solution containing solid particles of each of the catalysts in direct contact or near contact with each other. The solid particles, either between like and/or different compositions, may be unfused or fused. A solid solution without direct contact between the different types of catalyst particles can be established by, for example, incorporating particles of each type of catalyst in a common scaffold or support, while keeping the two types of catalyst in separated locations of the scaffold or support. The term "near contact", generally indicates no more than or less than 5 cm, 2 cm, 1 cm, or 0.5 cm distance between the two types of particles. The term "particles", as used herein, includes solid shapes of any suitable dimension, which may be in the nanometer range (e.g., 10, 20, 50, 100, 200, or 500 nm), micrometer range (e.g., 1, 2, 5, 10, 50, 100, or 500 microns), or macroscale range (e.g., 1, 2, 5, 10, 20, or 50 mm), or a dimension within a range bounded by any two of the foregoing exemplary values.

In the single-step process, hydrocarbon generated from reaction of the alcohol with the metal-loaded zeolite is instantaneously reacted with the alkylation catalyst included in the combination catalyst as hydrocarbon is formed. The single-step process may utilize any of the temperature and other processing conditions described above for the two-stage process. Moreover, the single-step process may or may not include any one or more additional processes, such as those exemplified above.

The alkylated benzene portion produced by reaction of the hydrocarbon fraction and alkylation catalyst includes one or a mixture of any of the alkylated benzene compounds that can be produced by the alkylation process. Some specific examples of alkylated benzene product include the ethylbenzenes, isopropylbenzenes (e.g., cumene (isopropylbenzene), diisopropylbenzenes, and triisopropylbenzenes), and butylbenzenes. Typically, at least a portion of the alkylated benzene product is ethylated benzene, which can be, for example, mono-, di-, or tri-ethylated benzene. The ethylbenzenes are generally produced by reaction of benzene with ethylene, wherein ethylene is generally produced during the conversion process. Similarly, other higher alkylbenzenes are generally produced by reaction of benzene with higher alkenes (e.g., propylene, butene, pentene, hexene) formed in the conversion process. Since other unsaturated or aromatic compounds aside from benzene (e.g., toluene, the xylenes, trimethylbenzenes, biphenyl, naphthalene, anthracene, phenanthrene, cyclobutene, cyclopentene, and cyclohexene, and methylated derivatives thereof) are also generally produced in the conversion process, the alkylation process generally results in the production of other alkylated aromatics and alkylated polycyclics (e.g., ethyltoluenes, ethylxylenes, ethylnapthalenes, ethylcyclobutenes, and ethylcyclopentenes, and methylated derivatives thereof). Any of these alkylated aromatic or polycyclic compounds may be isolated for use as a commercially or industrially relevant product. Alternatively, any of these alkylated aromatic or polycyclic compounds may be further reacted (e.g., with an alkene feed under alkylation conditions) to form a product of commercial or industrial relevance. Since cyclic unsaturated or aromatic compounds other than benzene are generally also alkylated by the alkylation process used herein, the method can be said to reduce the content of not only benzene, but also other non-alkylated cyclic unsaturated or aromatic compounds as well.

The term "reduced in benzene content", as used herein, means that the benzene content in the hydrocarbon fraction after reaction with the alkylation catalyst is lower than the benzene content in the hydrocarbon fraction before reaction with the alkylation catalyst (in a two-stage process) or without the alkylation catalyst (in a one-step process using a catalyst mixture). In different embodiments, the benzene content in the hydrocarbon fraction directly after reaction with the alkylation catalyst, or after reaction with a mixture of the two catalysts, is precisely, about, up to, or less than, for example, 4, 3, 2, 1, 0.8, 0.7, 0.6, 0.5, 0.4, 0.3, 0.2, or 0.1% by volume of the hydrocarbon fraction. In a particular embodiment, the benzene content in the hydrocarbon fraction directly after reaction with the alkylation catalyst is no more than or less than 0.62% by volume of the hydrocarbon fraction, in accordance with existing EPA regulations. In other embodiments, the amount of benzene is substantially or completely absent (i.e., up to or less than 0.05%, 0.02%, 0.01%, or even 0%). In some embodiments, the term "reduced in benzene content" can also mean "reduced in non-alkylated cyclic unsaturated compounds" or "reduced in non-alkylated aromatic compounds", wherein any of the exemplary percentages by volume provided for benzene content can alternatively be taken as content of non-alkylated cyclic unsaturated compounds or content of non-alkylated aromatic compounds.

In some embodiments, the conversion method described above is integrated with a fermentation process, wherein the fermentation process produces the alcohol used as feedstock for the conversion process. By being "integrated" is meant that alcohol produced at a fermentation facility or zone is sent to and processed at an alcohol-to-hydrocarbon conversion facility or zone that performs the conversion process described above. Preferably, in order to minimize production costs, the fermentation process is in close enough proximity to the conversion facility or zone, or includes appropriate conduits for transferring produced alcohol to the conversion facility or zone, thereby not requiring the alcohol to be shipped. In particular embodiments, the fermentation stream produced in the fermentation facility is directly transferred to the conversion facility, generally with removal of solids from the raw stream (generally by filtration or settling) before contact of the stream with the catalyst.

In some embodiments, the fermentation process is performed in an autonomous fermentation facility, i.e., where saccharides, produced elsewhere, are loaded into the fermentation facility to produce alcohol. In other embodiments, the fermentation process is part of a larger biomass reactor facility, i.e., where biomass is decomposed into fermentable saccharides, which are then processed in a fermentation zone. Biomass reactors and fermentation facilities are well known in the art. Biomass typically refers to lignocellulosic matter (i.e., plant material), such as wood, grass, leaves, paper, corn husks, sugar cane, bagasse, and nut hulls. Generally, biomass-to-ethanol conversion is performed by 1) pretreating biomass under well-known conditions to loosen lignin and hemicellulosic material from cellulosic material, 2) breaking down cellulosic material into fermentable saccharide material by the action of a cellulase enzyme, and 3) fermentation of the saccharide material, typically by the action of a fermenting organism, such as a suitable yeast.

In other embodiments, the alcohol is produced from a more direct sugar source, such as a plant-based source of sugars, such as sugar cane or a grain starch (such as corn starch). Ethanol production via corn starch (i.e., corn starch ethanol) and via sugar cane (i.e., cane sugar ethanol) currently represent some of the largest commercial production methods of ethanol. Integration of the instant conversion process with any of these large scale ethanol production methods is contemplated herein.

The alcohol-to-hydrocarbon conversion catalyst used herein includes a zeolite portion and a metal loaded into the zeolite (i.e., "metal-loaded zeolite"). The zeolite considered herein can be any of the porous aluminosilicate structures known in the art that are stable under high temperature conditions, i.e., of at least 100° C., 150° C., 200° C., 250° C., 300° C., and higher temperatures up to, for example, 500° C., 550° C., 600° C., 650° C., 700° C., 750° C., 800° C., 850° C., or 900° C. In particular embodiments, the zeolite is stable from at least 100° C. and up to 700° C. Typically, the zeolite is ordered by having a crystalline or partly crystalline structure, but amorphous forms may be also be useful. The zeolite can generally be described as a three-dimensional framework containing silicate ($SiO_2$ or $SiO_4$) and/or aluminate ($Al_2O_3$ or $AlO_4$) units that are interconnected (i.e., crosslinked) by the sharing of oxygen atoms.

The zeolite for the conversion process can be microporous (i.e., pore size of less than 2 μm), mesoporous (i.e., pore size within 2-50 μm, or sub-range therein), or a combination thereof. In several embodiments, the zeolite material is completely or substantially microporous. By being completely or substantially microporous, the pore volume due to micropores can be, for example, 100%, or at least 95%, 96%, 97%, 98%, 99%, or 99.5%, with the remaining pore volume being due to mesopores, or in some embodiments, macropores (pore size greater than 50 μm). In other embodiments, the zeolite material is completely or substantially mesoporous. By being completely or substantially mesoporous, the pore volume due to mesopores can be, for example, 100%, or at least 95%, 96%, 97%, 98%, 99%, or 99.5%, with the remaining pore volume being due to micropores, or in some embodiments, macropores. In yet other embodiments, the zeolite material contains an abundance of both micropores and mesopores. By containing an abundance of both micropores and mesopores, the pore volume due to mesopores can be, for example, up to, at least, or precisely 50%, 60%, 70%, 80%, or 90%, with the pore volume balance being due to micropores, or vice-versa.

In various embodiments, the zeolite for the conversion process is a MFI-type zeolite, MEL-type zeolite, MTW-type zeolite, MCM-type zeolite, BEA-type zeolite, kaolin, or a faujasite-type of zeolite. Some particular examples of zeolites include the ZSM class of zeolites (e.g., ZSM-5, ZSM-8, ZSM-11, ZSM-12, ZSM-15, ZSM-23, ZSM-35, ZSM-38, ZSM-48), zeolite X, zeolite Y, zeolite beta, and the MCM class of zeolites (e.g., MCM-22 and MCM-49). The compositions, structures, and properties of these zeolites are well-known in the art, and have been described in detail, as found in, for example, U.S. Pat. Nos. 4,721,609, 4,596,704, 3,702,886, 7,459,413, and 4,427,789, the contents of which are incorporated herein by reference in their entirety.

The zeolite for the conversion process can have any suitable silica-to-alumina (i.e., $SiO_2/Al_2O_3$ or "Si/Al") ratio. For example, in various embodiments, the zeolite can have a Si/Al ratio of precisely, at least, less than, or up to 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 120, 150, or 200, or a Si/Al ratio within a range bounded by any two of the foregoing values. In particular embodiments, the zeolite possesses a Si/Al ratio of 1 to 45.

In particular embodiments, the zeolite for the conversion process is ZSM-5. ZSM-5 belongs to the pentasil-containing class of zeolites, all of which are also considered herein. In particular embodiments, the ZSM-5 zeolite is represented by the formula $Na_nAl_nSi_{96-n}O_{192} \cdot 16H_2O$, wherein $0<n<27$.

Typically, the zeolite contains an amount of cationic species. As is well known in the art, the amount of cationic species is generally proportional to the amount of aluminum in the zeolite. This is because the replacement of silicon atoms with lower valent aluminum atoms necessitates the presence of countercations to establish a charge balance. Some examples of cationic species include hydrogen ions ($H^+$), alkali metal ions, alkaline earth metal ions, and main group metal ions. Some examples of alkali metal ions that may be included in the zeolite include lithium ($Li^+$), sodium ($Na^+$), potassium ($K^+$), rubidium ($Rb^+$), and cesium ($Cs^+$). Some examples of alkaline earth metal ions that may be included in the zeolite include ($Be^{2+}$), magnesium ($Mg^{2+}$), calcium ($Ca^{2+}$), strontium ($Sr^{2+}$), and barium ($Ba^{2+}$). Some examples of main group metal ions that may be included in the zeolite include boron ($B^{3+}$), gallium ($Ga^{3+}$), indium ($In^{3+}$), and arsenic ($As^{3+}$). In some embodiments, a combination of cationic species is included. The cationic species can be in a trace amount (e.g., no more than 0.01 or 0.001%), or alternatively, in a significant amount (e.g., above 0.01%, and up to, for example, 0.1, 0.5, 1, 2, 3, 4, or 5% by weight of the zeolite).

In some embodiments, any one or more of the above classes or specific examples of cationic species are excluded from the zeolite.

The zeolite described above is loaded with an amount of catalytically active metal. The type and amount of catalytic metal loaded into the zeolite are selected such that the resulting metal-loaded zeolite is catalytically active, under conditions set forth above, for converting an alcohol to a hydrocarbon. Typically, the metal considered herein is in the form of positively-charged metal ions (i.e., metal cations). The metal cations can be, for example, monovalent, divalent, trivalent, tetravalent, pentavalent, or hexavalent. In some embodiments, the metal is (or includes) alkali metal ions. In other embodiments, the metal is (or includes) alkaline earth metal ions. In other embodiments, the metal is (or includes) a transition metal, such as one or more first, second, or third row transition metals. Some preferred transition metals include copper, iron, zinc, titanium, vanadium, and cadmium. The copper ions can be cuprous ($Cu^{+1}$) or cupric ($Cu^{+2}$) in nature, and the iron atoms can be ferrous ($Fe^{+2}$) or ferric ($Fe^{+3}$) in nature. Vanadium ions may be in any of its known oxidation states, e.g., $V^{+2}$, $V^{+3}$, $V^{+4}$, and $V^{+5}$. In other embodiments, the metal is (or includes) a catalytically active main group metal, such as gallium or indium. A single metal or a combination of metals may be loaded into the zeolite. In other embodiments, any one or more metals described above are excluded from the zeolite.

The loading of catalytic metal in the zeolite can be any suitable amount, but is generally no more than about 2.5%, wherein the loading is expressed as the amount of metal by weight of the zeolite. In different embodiments, the metal loading is precisely, at least, less than, or up to, for example, 0.01%, 0.02%, 0.03%, 0.04%, 0.05%, 0.06%, 0.07%, 0.08%, 0.09%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, or 2.5%, or a metal loading within a range bounded by any two of the foregoing values.

In further aspects of the invention, the zeolite catalyst may include at least one trivalent metal ion in addition to one or more metals described above. As used herein, the term "trivalent metal ion" is defined as a trivalent metal ion other than aluminum ($Al^{+3}$). Without wishing to be bound by any theory, it is believed that the trivalent metal is incorporated into the zeolite structure. More specifically, the incorporated trivalent metal ion is believed to be bound in the zeolite to an appropriate number of oxygen atoms, i.e., as a metal oxide unit containing the metal cation connected to the structure via oxygen bridges. In some embodiments, the presence of a trivalent metal ion in combination with one or more other catalytically active metal ions may cause a combined effect different than the cumulative effect of these ions when used alone. The effect primarily considered herein is on the resulting catalyst's ability to convert alcohols into hydrocarbons.

In some embodiments, only one type of trivalent metal ion aside from aluminum is incorporated into the zeolite. In other embodiments, at least two types of trivalent metal ions aside from aluminum are incorporated into the zeolite. In yet other embodiments, at least three types of trivalent metal ions aside from aluminum are incorporated into the zeolite. In yet other embodiments, precisely two or three types of trivalent metal ions aside from aluminum are incorporated into the zeolite.

Each of the trivalent metal ions can be included in the zeolite in any suitable amount, such as, precisely, at least, less than, or up to, for example, 0.01%, 0.02%, 0.03%, 0.04%, 0.05%, 0.06%, 0.07%, 0.08%, 0.09%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, or 2.5%, or an amount within a range bounded by any two of the foregoing values. Alternatively, the total amount of trivalent metal ions (other than Al) may be limited to any of the foregoing values. In some embodiments, one or more specific types, or all, trivalent metal ions other than Al are excluded from the catalyst.

In a first set of embodiments, at least one trivalent metal ion is selected from trivalent transition metal ions. The one or more transition metals can be selected from any or a select portion of the following types of transition metals: elements of Groups IIIB (Sc group), IVB (Ti group), VB (V group), VIB (Cr group), VIIB (Mn group), VIIIB (Fe and Co groups) of the Periodic Table of the Elements. Some examples of trivalent transition metal ions include $Sc^{+3}$, $Y^{+3}$, $V^{+3}$, $Nb^{+3}$, $Cr^{+3}$, $Fe^{+3}$, and $Co^{+3}$. In other embodiments, the trivalent metal ion excludes all transition metal ions, or alternatively, excludes any one, two, or more classes or specific examples of transition metal ions provided above. In particular embodiments, the trivalent transition metal ions include $Sc^{+3}$, or $Fe^{+3}$, or a combination thereof.

In a second set of embodiments, at least one trivalent metal ion is selected from trivalent main group metal ions. The one or more main group metals can be selected from any or a select portion of elements of Group IIIA (B group) and/or Group VA (N group) of the Periodic Table, other than aluminum. Some examples of trivalent main group metal ions include $Ga^{+3}$, $In^{+3}$, $As^{+3}$, $Sb^{+3}$, and $Bi^{+3}$. In other embodiments, the trivalent metal ion excludes all main group metal ions other than aluminum, or alternatively, excludes any one, two, or more classes or specific examples of main group metal ions provided above. In particular embodiments, the trivalent main group metal ions include at least $In^{3+}$.

In a third set of embodiments, at least one trivalent metal ion is selected from trivalent lanthanide metal ions. Some examples of trivalent lanthanide metal ions considered herein include $La^{+3}$, $Ce^{+3}$, $Pr^{+3}$, $Nd^{+3}$, $Sm^{+3}$, $Eu^{+3}$, $Gd^{+3}$, $Tb^{+3}$, $Dy^{+3}$, $Ho^{+3}$, $Er^{+3}$, $Tm^{+3}$, $Yb^{+3}$, and $Lu^{+3}$. In particular embodiments, the trivalent lanthanide metal ion is selected from one or a combination of $La^{+3}$, $Ce^{+3}$, $Pr^{+3}$, and $Nd^{+3}$. In further particular embodiments, the trivalent lanthanide metal ion is or includes $La^{+3}$. In other embodiments, the trivalent metal ion excludes all lanthanide metal ions, or alternatively, excludes any one, two, or more classes or specific examples of lanthanide metal ions provided above.

In a fourth set of embodiments, the zeolite includes at least two trivalent metal ions selected from trivalent transition metal ions. Some combinations of trivalent transition metal ions considered herein include $Sc^{+3}$ in combination with one or more other trivalent transition metal ions, or $Fe^{+3}$ in combination with one or more other trivalent transition metal ions, or $Y^{+3}$ in combination with one or more other trivalent transition metal ions, or $V^{+3}$ in combination with one or more other trivalent transition metal ions.

In a fifth set of embodiments, the zeolite includes at least two trivalent metal ions selected from trivalent main group metal ions. Some combinations of trivalent main group metal ions considered herein include $In^{+3}$ in combination with one or more other trivalent main group metal ions, or $Ga^{+3}$ in combination with one or more other trivalent main group metal ions, or $As^{+3}$ in combination with one or more other trivalent main group metal ions.

In a sixth set of embodiments, the zeolite includes at least two trivalent metal ions selected from trivalent lanthanide metal ions. Some combinations of trivalent lanthanide metal ions considered herein include $La^{+3}$ in combination with one or more other trivalent lanthanide metal ions, or $Ce^{+3}$ in combination with one or more other trivalent lanthanide metal ions, or $Pr^{+3}$ in combination with one or more other trivalent lanthanide metal ions, or $Nd^{+3}$ in combination with one or more other trivalent lanthanide metal ions.

In a seventh set of embodiments, the zeolite includes at least one trivalent transition metal ion and at least one trivalent lanthanide metal ion. For example, in particular embodiments, at least one trivalent metal ion is selected from $Sc^{+3}$, $Fe^{+3}$, $V^{+3}$, and/or $Y^{+3}$, and another trivalent metal ion is selected from $La^{+3}$, $Ce^{+3}$, $Pr^{+3}$, and/or $Nd^{+3}$.

In an eighth set of embodiments, the zeolite includes at least one trivalent transition metal ion and at least one trivalent main group metal ion. For example, in particular embodiments, at least one trivalent metal ion is selected from $Sc^{+3}$, $Fe^{+3}$, $V^{+3}$, and/or $Y^{+3}$, and another trivalent metal ion is selected from $In^{+3}$, $Ga^{+3}$, and/or $In^{+3}$.

In a ninth set of embodiments, the zeolite includes at least one trivalent main group metal ion and at least one trivalent lanthanide metal ion. For example, in particular embodiments, at least one trivalent metal ion is selected from $In^{+3}$, $Ga^{+3}$, and/or $In^{+3}$, and another trivalent metal ion is selected from $La^{+3}$, $Ce^{+3}$, $Pr^{+3}$, and/or $Nd^{+3}$.

In a tenth set of embodiments, the zeolite includes at least three trivalent metal ions. The at least three trivalent metal ions can be selected from trivalent transition metal ions, trivalent main group metal ions, and/or trivalent lanthanide metal ions.

In particular embodiments, one, two, three, or more trivalent metal ions are selected from $Sc^{+3}$, $Fe^{+3}$, $Y^{-3}$, $Y^{+3}$, $La^{+3}$, $Ce^{+3}$, $Pr^{+3}$, $Nd^{+3}$, $In^{+3}$, and/or $Ga^{+3}$. In more particular embodiments, one, two, three, or more trivalent metal ions are selected from $Sc^{+3}$, $Fe^{+3}$, $V^{+3}$, $La^{+3}$, and/or $In^{+3}$.

In particular embodiments, the zeolite catalyst is or includes a pentasil-type composition loaded with any of the suitable metals described above. In more specific embodiments, the zeolite catalyst is, or includes, for example, copper-loaded ZSM5 (i.e., Cu-ZSM5), Fe-ZSM5, Cu,Fe-ZSM5, or a mixture of Cu-ZSM5 and Fe-ZSM5. In other embodiments, the zeolite catalyst is, or includes, for example, Cu—La-ZSM5, Fe—La-ZSM5, Fe—Cu—La-ZSM5, Cu—Sc-ZSM5, or Cu—In-ZSM5.

The zeolite catalyst described above is typically not coated with a metal-containing film or layer. However, the instant invention may or may not also include that the zeolite catalyst described above is coated with a metal-containing film or layer, as long as the film or layer does not substantially impede the catalyst from effectively functioning as a conversion catalyst, as intended herein. By being coated, the film or layer resides on the surface of the zeolite. In some embodiments, the surface of the zeolite refers to only the outer surface (i.e., as defined by the outer contour area of the zeolite catalyst), while in other embodiments, the surface of the zeolite refers to or includes inner surfaces of the zeolite, such as the surfaces within pores or channels of the zeolite. The metal-containing film or layer can serve, for example, to adjust the physical characteristics of the catalyst, the catalytic efficiency, or catalytic selectivity. Some examples of metal-containing surfaces include the oxides and/or sulfides of the alkali metals, alkaline earth metals, and divalent transition or main group metals, provided that such surface metals are non-contaminating to the hydrocarbon product and non-deleterious to the conversion process.

The metal-loaded zeolite described herein can be synthesized by any suitable method known in the art. The method considered herein should preferably incorporate the metal ions homogeneously into the zeolite. The zeolite may be a single type of zeolite, or a combination of different zeolite materials.

In particular embodiments, the metal-loaded zeolite described herein is prepared by, first, impregnating the zeolite with the metals to be loaded. The impregnating step can be achieved by, for example, treating the zeolite with one or more solutions containing salts of the metals to be loaded. By treating the zeolite with the metal-containing solution, the metal-containing solution is contacted with the zeolite such that the solution is absorbed into the zeolite, preferably into the entire volume of the zeolite. Typically, in preparing the metal-loaded zeolite catalyst (e.g., Cu-ZSM5 or V-ZSM-5), the acid zeolite form (i.e., H-ZSM5) or its ammonium salt (e.g., $NH_4$-ZSM-5) is used as a starting material on which an exchange with metal ions (e.g., copper ions) is performed. The particulars of such metal exchange processes are well known in the art.

In one embodiment, the impregnating step is achieved by treating the precursor zeolite with a solution that contains all of the metals to be loaded. In another embodiment, the impregnating step is achieved by treating the precursor zeolite with two or more solutions, wherein the different solutions contain different metals or combinations of metals. Each treatment of the precursor zeolite with an impregnating solution corresponds to a separate impregnating step. Typically, when more than one impregnating step is employed, a drying and/or thermal treatment step is employed between the impregnating steps.

The metal-impregnating solution contains at least one or more metal ions to be loaded into the zeolite, as well as a liquid carrier for distributing the metal ions into the zeolite. The metal ions are generally in the form of metal salts. Preferably, the metal salts are completely dissolved in the liquid carrier. The metal salt contains one or more metal ions in ionic association with one or more counteranions. Any one or more of the metal ions described above can serve as the metal ion portion. The counteranion can be selected from, for example, halides ($F^-$, $Cl^-$, $Br^-$, or $I^-$), carboxylates (e.g., formate, acetate, propionate, or butyrate), sulfate, nitrate, phosphate, chlorate, bromate, iodate, hydroxide, β-diketonate (e.g., acetylacetonate), and dicarboxylates (e.g., oxalate, malonate, or succinate).

In particular embodiments, the metal-loaded zeolite is prepared by forming a slurry containing zeolite powder and the metals to be incorporated. The resulting slurry is dried and fired to form a powder. The powder is then combined with organic and/or inorganic binders and wet-mixed to form a paste. The resulting paste can be formed into any desired shape, e.g., by extrusion into rod, honeycomb, or pinwheel structures. The extruded structures are then dried and fired to form the final catalyst. In other embodiments, the zeolite powder, metals, and binders are all combined together to form a paste, which is then extruded and fired.

After impregnating the zeolite, the metal-loaded zeolite is typically dried and/or subjected to a thermal treatment step (e.g., a firing or calcination step). The thermal treatment step functions to permanently incorporate the impregnated metals into the zeolite, e.g., by replacing $Al^{+3}$ and/or $Si^{+4}$ and forming metal-oxide bonds within the zeolite material. In different embodiments, the thermal treatment step can be conducted at a temperature of at least 100° C., 150° C., 200° C., 250° C., 300° C., 350° C., 400° C., 450° C., 500° C., 550° C., 600° C., 650° C., 700° C., 750° C., or 800° C., or within a range therein, for a time period of, for example, 15 minutes, 30 minutes, 1 hour, 2 hours, 6 hours, 12 hours, 24 hours, 30 hours, 36 hours, or 48 hours, or within a range therein. In some particular embodiments, the thermal treatment step is conducted at a temperature of at least 500° C. for a time period of at least two hours. In some embodiments, the thermal treatment step includes a temperature ramping step from a lower temperature to a higher temperature, and/or from a higher temperature to a lower temperature. For example, the thermal treatment step can include a ramp stage from 100-700° C., or vice-versa, at a rate of 1, 2, 5, or 10° C./min.

Generally, the one or more heat treatment steps for producing the metal-loaded zeolite catalyst are conducted under normal atmospheric pressure. However, in some embodiments, an elevated pressure (e.g., above 1 atm and up to 2, 5, or 10 atm) is employed, while in other embodiments, a reduced pressure (e.g., below 1, 0.5, or 0.2 atm) is employed. Furthermore, although the heat treatment steps are generally conducted under a normal air atmosphere, in some embodiments, an elevated oxygen, reduced oxygen, or inert atmosphere is used. Some gases that can be included in the processing atmosphere include, for example, oxygen, nitrogen, helium, argon, carbon dioxide, and mixtures thereof.

For the sake of providing a more descriptive example, a Cu-ZSM-5 catalyst can be prepared as follows: 2.664 g of copper acetate hydrate (i.e., $Cu(OAc)_2.6H_2O$) is dissolved in 600 mL de-ionized water (0.015M), followed by addition of 10.005 g of H-ZSM-5 zeolite. The slurry is kept stirring for about two hours at 50° C. Cu-ZSM-5 (blue in color) is collected by filtration after cooling, washed with de-ionized water, and calcined in air at about 500° C. (10° C./min) for four hours.

The produced Cu-ZSM-5 precursor can then be further impregnated with another metal, such as iron. For example, Cu—Fe-ZSM-5 can be produced as follows: 5 g of Cu-ZSM-5 is suspended in an aqueous solution of 25 mL of 0.015M $Fe(NO_3)_3$, degassed with $N_2$, and is kept stirring for about two hours at about 80° C. Brown solid is obtained after filtration, leaving a clear and colorless filtrate. The product is then calcined in air at about 500° C. (2° C./min) for about two hours. The resulting Cu—Fe-ZSM-5 catalyst typically contains about 2.4% Cu and 0.3% Fe. Numerous other metals can be loaded into the zeolite by similar means to produce a variety of different metal-loaded catalysts. By another method, CuFe-ZSM-5 can also be prepared by an incipient wetness method. In this method, an amount of Cu-SSZ-13 (e.g., 10 g) can be ground with a suitable amount of Fe $(NO_3)_3.9H_2O$ (e.g., 0.3 g) and just enough water can be added to cover the surface of Cu-SSZ-13. The color of Cu-SSZ-13 typically changes slowly from green to yellow. The sample is then typically allowed to dry in air and then generally calcined in air at, for example, 500° C. (2° C./min) for about 4 hours to yield pale yellow CuFe-SSZ-13.

Generally, the zeolite catalyst described herein is in the form of a powder. In a first set of embodiments, at least a portion, or all, of the particles of the powder have a size less than a micron (i.e., nanosized particles). The nanosized particles can have a particle size of precisely, at least, up to, or less than, for example, 1, 2, 5, 10, 20, 30, 40, 50, 60, 70, 80, 90, 100, 150, 200, 250, 300, 350, 400, 450, 500, 550, 600, 650, 700, 750, 800, 850, 900, or 950 nanometers (nm), or a particle size within a range bounded by any two of the foregoing values. In a second set of embodiments, at least a portion, or all, of the particles of the powder have a size at or above 1 micron in size. The micron-sized particles can have a particle size of precisely, at least, up to, or less than, for example, 1, 2, 5, 10, 20, 30, 40, 50, 60, 70, 80, 90, or 100 microns (m), or a particle size within a range bounded by any two of the foregoing values. In some embodiments, single crystals or grains of the catalyst correspond to any of the sizes provided above, while in other embodiments, crystals or grains of the catalyst are agglomerated to provide agglomerated crystallites or grains having any of the above exemplary dimensions.

In other embodiments, the zeolite catalyst can be in the form of a film, a coating, or a multiplicity of films or coatings. The thickness of the coatings or multiplicity of coatings can be, for example, 1, 2, 5, 10, 50, or 100 microns, or a range therein, or up to 100 micron thickness. In yet other embodiments, the zeolite catalyst is in the form of a non-particulate (i.e., continuous) bulk solid. In still other embodiments, the zeolite catalyst can be fibrous or in the form of a mesh.

The benzene alkylation catalyst can be any of the benzene alkylation catalysts known in the art. In a one-step process in which a catalyst mixture is used, the benzene alkylation catalyst is generally a solid, and typically in the form of particles, in order to form a solid solution of the conversion and alkylation catalysts. In a two-step process in which the two catalysts are separate, the benzene alkylation catalyst can be any of the benzene alkylation catalysts known in the art, including solid and liquid (and solid-liquid) alkylation catalysts.

In a first embodiment, the benzene alkylation catalyst is a zeolite catalyst. Any of the zeolite catalysts described above that may possess benzene alkylation activity could be used as an alkylation catalyst herein, provided that the alkylation catalyst has a composition different than the conversion catalyst. Some examples of zeolite-based alkylation catalysts include zeolite Y, Ca-zeolite Y, mordenite, MCM (e.g., MCM-22, MCM-41, MCM-48, MCM-49, MCM-56, MCM-58, or MCM-68), ZSM-5, ZSM-11, and zeolite beta catalysts, as well as combinations thereof, and phosphate modified forms thereof. The zeolite-based alkylation catalysts are often in their ammonium (e.g., $NH_4^+$), hydrogen, or alkali metal forms, although heavier metal-loaded forms (e.g., Al, Zr, Fe, and other metal forms, as above) are also used. In the particular case of a ZSM-5 catalyst, the catalyst may be exchanged in some cases with H, La, Mg, Pt, or Zn.

In a second embodiment, the alkylation catalyst is a Friedel-Crafts type of catalyst. Some examples of Friedel-Crafts types of catalysts include mixtures of $AlCl_3$ and HCl (for which the alkylation process is generally practiced below 135° C. and at sufficient pressure to keep the reactants in the liquid phase), a composite of phosphoric acid and a solid binder material, such as kieselguhr or diatomaceous earth (for which the alkylation process is generally practiced in a fixed bed reactor at 180-240° C.), hydrogen fluoride (HF), and boron trifluoride ($BF_3$), wherein the latter two may be in gaseous form, in solution, or in adduct form (e.g., etherate). Other Friedel-Crafts catalysts include $SbCl_5$, $FeCl_3$, and $AlBr_3$. The alkylation process using a Friedel-Crafts catalyst may or may not further include an alkyl halide that functions to alkylate the benzene and other aromatic compounds.

The process conditions (e.g., temperature and pressure) generally employed with benzene alkylation catalysts are well known in the art. In some embodiments, the conditions used for treating the hydrocarbon fraction with the benzene alkylation catalyst can be any of the conditions provided supra for the conversion process.

In particular embodiments, the conversion catalyst and alkylation catalyst are selected in a manner that tunes the fractionation of the end hydrocarbon product toward a higher boiling fraction. The higher boiling fraction is preferably one that mimics a diesel jet or gasoline fuel.

When a mixture of catalysts is used, any suitable weight ratio of the alcohol conversion catalyst and alkylation catalyst (with respect to the total amount of catalyst) can be used. In different embodiments, the alkylation catalyst is included in an amount of precisely, about, at least, above, up to, or less than, for example, 1, 2, 5, 10, 15, 20, 25, 30, 35, 40, 45, 50, 55, 60, 65, or 70 wt % with respect to the total weight of the catalyst mixture. The alkylation catalyst may also be included within a range of any of the foregoing exemplary values, such as in an amount of 5-50 wt %.

Any of the catalysts described above, if appropriate, may be mixed with or affixed onto a support material. The support material can be a powder (e.g., having any of the above particle sizes), granular (e.g., 0.5 mm or greater particle size), a bulk material, such as a honeycomb monolith of the flow-through type, a plate or multi-plate structure, or corrugated metal sheets. If a honeycomb structure is used, the honeycomb structure can contain any suitable density of cells. For example, the honeycomb structure can have 100, 200, 300, 400, 500, 600, 700, 800, or 900 cells per square inch (cells/in$^2$) (or from 62-140 cells/cm$^2$) or greater. The support material is generally constructed of a refractory composition, such as those containing cordierite, mullite, alumina (e.g., α-, β-, or γ-alumina), or zirconia, or a combination thereof. Honeycomb structures, in particular, are described in detail in, for example, U.S. Pat. Nos. 5,314,665, 7,442,425, and 7,438,868, the contents of which are incorporated herein by reference in their entirety. When corrugated or other types of metal sheets are used, these can be layered on top of each other with catalyst material supported on the sheets such that passages remain that allow the flow of alcohol-containing fluid or hydrocarbon gas. The layered sheets can also be formed into a structure, such as a cylinder, by winding the sheets.

Examples have been set forth below for the purpose of illustration and to describe certain specific embodiments of the invention. However, the scope of this invention is not to be in any way limited by the examples set forth herein.

EXAMPLE 1

Ethanol Conversion Over a Mixture of V-ZSM-5 and Zeolite-Y

Figure 1:
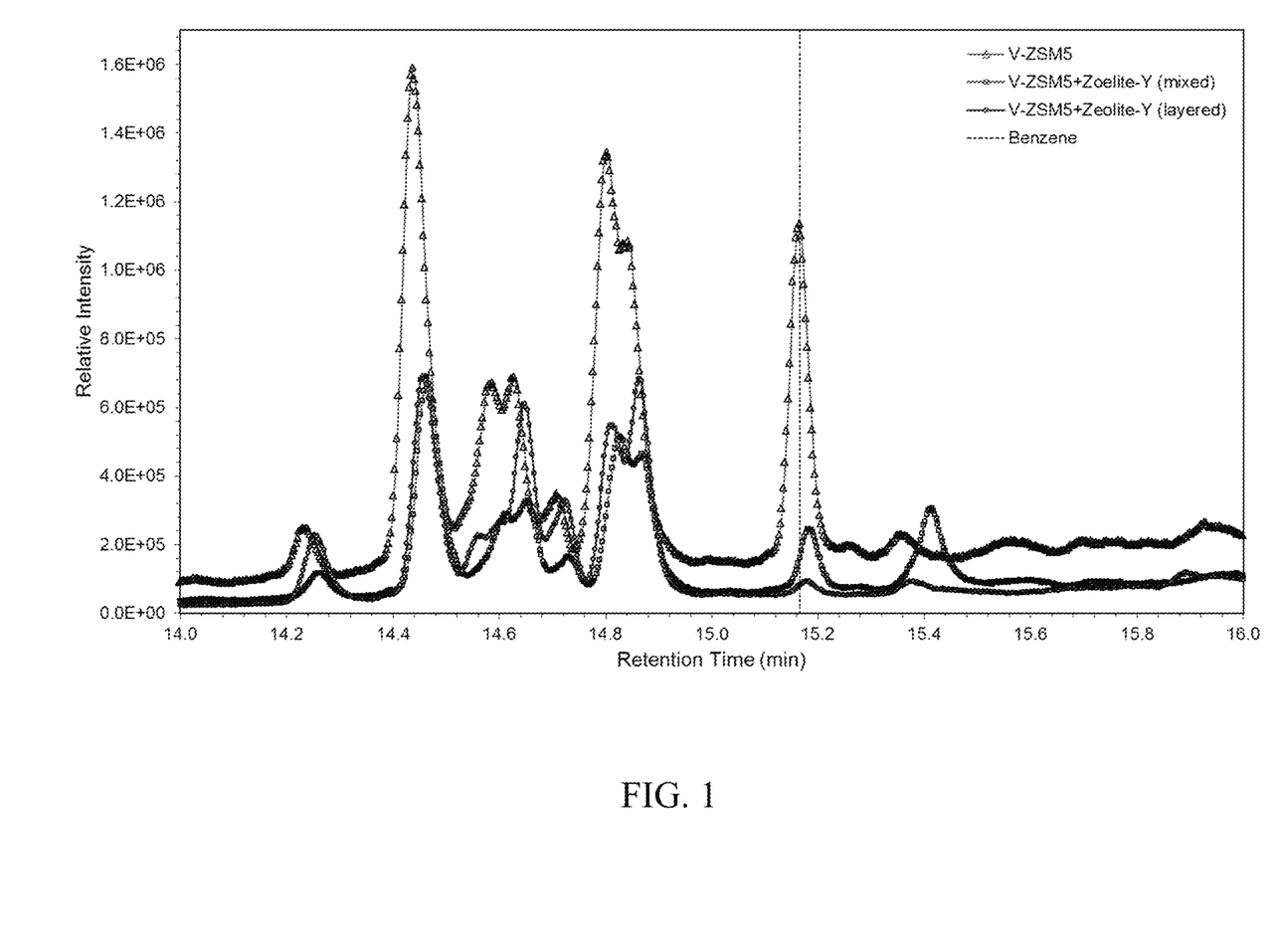
FIG. 1. Gas chromatogram of product stream from ethanol conversion over V-ZSM-5, mixture of V-ZSM-5+Zeolite-Y, and Zeolite-Y dowsteam of V-ZSM-5 ("V-ZSM-5+Zeolite-Y layered").

The mixed catalyst was prepared by mechanically mixing 150 mg of V-ZSM5 with 50 mg Zeolite-Y, and the catalyst loaded onto a tube reactor. An ethanol stream flowing at a rate of 1.0 mL (LHSV of 2.93 h$^{-1}$) and diluted with a helium at a flow of 50 mL/minute was passed over the catalyst mixture at 350° C. and atmospheric pressure. The reaction was allowed to run for 60 minutes to ensure steady state, and the product stream was analyzed by GC-MS. The chromatogram of the product stream for a relevant retention time of 14-16 minutes is shown in FIG. 1. For comparison, the chromatogram of the product stream from V-ZSM-5 is also shown. The dotted black line shows the position for the benzene peak, which is present in the product stream from the reaction over V-ZSM-5 but is absent in the product stream from reaction over the mixture of V-ZSM-5 and Zeolite-Y catalysts. The analysis of the product stream also shows that $C_3$-$C_8$ hydrocarbons decrease and $C_9$-$C_{10}$ hydrocarbons increase when Zeolite-Y is mixed with V-ZSM-5.

EXAMPLE 2

Ethanol Conversion Over V-ZSM-5 with Downstream Zeolite-Y

The catalyst loading was configured such that a 50 mg of Zeolite-Y was loaded on a reactor downstream of 200 mg of V-ZSM-5. An ethanol stream flowing at a rate of 1.0 mL (LHSV of 2.93 h$^{-1}$) and diluted with helium at a flow of 50 mL/minute was passed over the catalyst system at 350° C. and atmospheric pressure. In this configuration, ethanol converts to hydrocarbon stream over V-ZSM-5, and the hydrocarbon stream is passed over Zeolite-Y. The reaction was allowed to run for 60 minutes to ensure steady state, and the product stream was analyzed by GC-MS. The chromatogram of the product stream for a relevant retention time of 14-16 minutes is comparatively shown in FIG. 1. The dotted black line shows the position for the benzene peak, which is present in the product stream from the reaction over V-ZSM-5 but is absent in the product stream from reaction when Zeolite-Y is downstream of V-ZSM-5.

Figure 2:
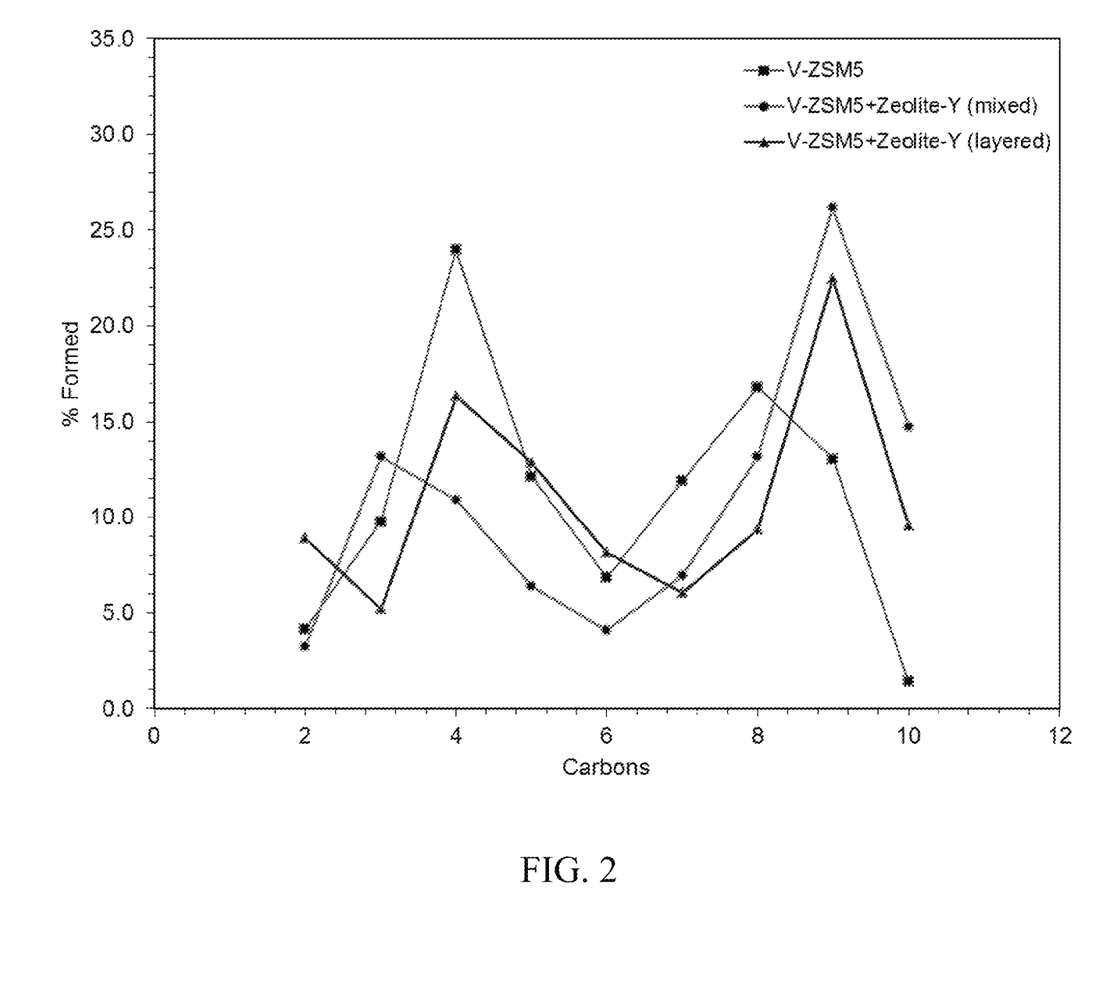
FIG. 2. Graph plotting the number of carbons atoms in product stream from ethanol conversion over V-ZSM-5, mixture of V-ZSM-5+Zeolite-Y, and Zeolite-Y dowsteam of V-ZSM-5 ("V-ZSM-5+Zeolite-Y layered").

FIG. 2 plots the carbon atom number distribution for the ethanol conversion over V-ZSM-5, mixture of V-ZSM-5 and Zeolite-Y, and Zeolite-Y downstream of V-ZSM-5 (i.e., "V-ZSM-5+Zeolite-Y layered"). The analysis of the product stream shows that $C_4$-$C_8$ hydrocarbons decrease and $C_9$-$C_{10}$ hydrocarbons increase when Zeolite-Y is downstream of V-ZSM-5 as compared with the product stream with only V-ZSM-5 as a catalyst.

While there have been shown and described what are at present considered the preferred embodiments of the invention, those skilled in the art may make various changes and modifications which remain within the scope of the invention defined by the appended claims.

What is claimed is:

1. A catalyst composition for converting an alcohol to a hydrocarbon, the catalyst composition comprising a mixture of (i) a vanadium-loaded pentasil zeolite catalyst catalytically active for converting said alcohol to said hydrocarbon, and (ii) a benzene alkylation catalyst selected from zeolite Y, mordenite, and MCM catalysts active for alkylating benzene.

2. The catalyst composition of claim 1, wherein said pentasil zeolite is comprised of ZSM5.

3. The catalyst composition of claim 1, wherein said benzene alkylation catalyst is zeolite Y.

4. A method for converting an alcohol to a hydrocarbon fraction having a lowered benzene content, the method comprising: converting said alcohol to a hydrocarbon fraction by contacting said alcohol, under conditions suitable for converting said alcohol to said hydrocarbon fraction, with a catalyst composition comprising a mixture of (i) a vanadium-loaded pentasil zeolite catalyst catalytically active for converting said alcohol to said hydrocarbon fraction, and (ii) a benzene alkylation catalyst selected from zeolite Y, mordenite, and MCM catalysts active for alkylating benzene, under conditions suitable for alkylating benzene, to form alkylated benzene product in said hydrocarbon fraction.

5. The method of claim 4, wherein said pentasil zeolite is comprised of ZSM5.

6. The method of claim 4, wherein said hydrocarbon fraction, after being processed with said benzene alkylation catalyst, has no more than 0.62% benzene by volume of the hydrocarbon fraction.

7. The method of claim 4, wherein said alcohol is comprised of ethanol.

8. The method of claim 4, wherein said alcohol is a component of an aqueous solution in a concentration of no more than about 20%.

9. The method of claim 8, wherein said alcohol is a component of a fermentation stream when contacted with said vanadium-loaded pentasil zeolite catalyst.

10. The method of claim 4, wherein said hydrocarbon fraction is useful as a fuel or as a blendstock component of a fuel.

11. The method of claim 4, wherein said method is integrated with a fermentation process, wherein said fermentation process produces said alcohol as a component of a fermentation stream, and said fermentation stream is contacted with said vanadium-loaded pentasil zeolite catalyst.

12. The method of claim 4, wherein said method is integrated with a biomass reactor that includes a fermentation process, wherein said fermentation process produces said alcohol as a component of a fermentation stream, and said fermentation stream is contacted with said vanadium-loaded pentasil zeolite catalyst.

\* \* \* \* \*